(12) United States Patent
Jain et al.

(10) Patent No.: US 7,781,622 B2
(45) Date of Patent: Aug. 24, 2010

(54) PROCESS FOR DIRECT HYDROXYLATION OF AROMATIC HYDROCARBONS

(75) Inventors: Suman Lata Jain, Uttarakhand (IN); Jomy K. Joseph, Uttarakhand (IN); Sweety Singhal, Uttarakhand (IN); Bir Sain, Uttarakhand (IN); Ragunathan Sivakumaran, Uttarakhand (IN); Basant Kumar, Uttarakhand (IN)

(73) Assignee: Council of Scientific & Industrial Research, Rafi Marg, New Delhi (IN)

( * ) Notice: Subject to any disclaimer, the term of this patent is extended or adjusted under 35 U.S.C. 154(b) by 51 days.

(21) Appl. No.: 12/261,351

(22) Filed: Oct. 30, 2008

(65) Prior Publication Data

US 2009/0192337 A1    Jul. 30, 2009

(30) Foreign Application Priority Data

Jan. 25, 2008    (IN) .......................... 204/08

(51) Int. Cl.
*C07C 37/60*    (2006.01)
*C07C 41/26*    (2006.01)

(52) U.S. Cl. ...................... 568/803; 568/629

(58) Field of Classification Search ............ None
See application file for complete search history.

(56) References Cited

U.S. PATENT DOCUMENTS

| 4,223,165 A | 9/1980 | Jouffret |
| 4,301,307 A | 11/1981 | Jouffret |
| 5,110,995 A | 5/1992 | Kharitonov et al. |
| 5,426,244 A | 6/1995 | Sugai et al. |
| 5,981,764 A | 11/1999 | Maekawa et al. |
| 6,180,836 B1 | 1/2001 | Cheng et al. |
| 6,476,277 B2 | 11/2002 | Vogil et al. |

FOREIGN PATENT DOCUMENTS

| DE | 19634406 A1 | 3/1998 |
| EP | 314583 A1 | 5/1989 |
| EP | 889081 A1 | 1/1999 |

OTHER PUBLICATIONS

Database CAPLUS on STN, Acc. No. 1963:52578, Kropf, Tetrahedron Letters (1962), p. 577-582 (abstract).*

* cited by examiner

*Primary Examiner*—Brian J Davis
(74) *Attorney, Agent, or Firm*—Leudeka, Neely & Graham, PC

(57) ABSTRACT

The present invention provides a process for direct hydroxylation of aromatic hydrocarbons like benzene to phenol, toluene to cresols and anisole to methoxy phenols by using hydrogen peroxide as environmentally benign oxidant in polar solvent like acetonitrile using vanadium phthalocyanine or its derivative as a catalyst, at a temperature in the range of 25-100° C.

13 Claims, No Drawings

PROCESS FOR DIRECT HYDROXYLATION OF AROMATIC HYDROCARBONS

FIELD OF THE INVENTION

The present invention relates to a process for direct hydroxylation of aromatic hydrocarbons. Particularly the present invention relates to a process for direct liquid phase hydroxylation of aromatic hydrocarbons with hydrogen peroxide catalyzed by vanadium based catalysts. More particularly the present invention relates to a process for direct liquid phase hydroxylation of aromatics like benzene to phenol, toluene to cresols and anisole to methoxyphenols by using hydrogen peroxide as environmentally benign oxidant in polar solvent like acetonitrile using vanadyl phthalocyanine as catalyst in the temperature range ambient to 100° C.

BACKGROUND OF THE PRESENT INVENTION

Hydroxy aromatics are valuable organic intermediates in chemical industries related to resin, plastics, pharmaceuticals and agrochemicals. Phenol for example is further processed to form phenol resins, caprolactam, bisphenol A, adipic acid. Similarly cresols are used for preparing antioxidants, herbicides, insecticides, dyes, flavoring agents, plastics and lubricating oils. p-Cresols is also used for producing BHT (2,6-di-tert-butyl-4-hydroxy toluene) an important antioxidant. Guaiacol (o-methoxyphenol) and p-methoxyphenol also find wide applications in the field of pharmaceuticals, synthetic perfumes, antioxidants and polymerization inhibitors.

There are a number of processes for preparing hydroxyaromatics. Phenol is conventionally produced from benzene via cumene process which involves alkylation of benzene with propylene to yield cumene, oxidation of cumene to cumene hydroperoxide by air and its cleavage in acidic medium to equimolar amounts of phenol and acetone. This process has several limitations such as multistep synthesis, generation of acetone as inevitable side product and lower yields of phenol. Cresol is produced from toluene by multistep reaction involving sulphonation, chlorination or by vapour phase methylation of phenol. In the first process toluene is sulphonated with concentrated sulphuric acid and the sodium salt of sulphonated toluene is fused with sodium hydroxide at 300° C. to yield a mixture of o-, m-, and p-cresols. The p-cresol is separated from the mixture by traditional crystallization. The process has disadvantages that large amount of sodium sulphite is produced as byproduct. Second process involves chlorination of toluene with sulphur dichloride in the presence of iron chloride, separation of chlorotoluene isomers followed by hydrolysis and distillation to yield pure o-, m-, and p-cresols. The process has the disadvantages like low yields of p-cresol, production of byproducts such as tolyl cresols and tolyl ethers. Cresol synthesis by vapor phase methylation of phenol yields only o-cresols and 2,6-xylenol, uses relatively expensive raw material phenol and require high capital cost corrosion resistant plant.

There are mainly two industrial processes for the production of guaiacol involving methylation of catechol with dimethyl sulphate or carbonate in presence of alkali. p-Methoxyphenol is industrially produced by selective methylation of hydroquinone with dimethyl sulphate or carbonate. These processes are highly environmentally unacceptable.

The one step process for direct hydroxylation of aromatic hydrocarbons has therefore attracted word wide attention and several methods for direct hydroxylation of benzene to phenol, toluene to cresols and anisole to guaiacol, p-methoxyphenol have been reported in the literature. There are many references in the prior art for direct hydroxylation of aromatics to hydroxyl aromatics and the important ones are discussed here.

A process using ZSM-5 as catalyst and $N_2O$ as oxidant has been reported for one step hydroxylation of benzene to phenol (J. Mol. Catal. 1993, 84, 117; Appl. Catal. A: Gen. 1992, 86, 139; Appl. Catal. A: Gen 1994, 117, 1). The main limitations for industrial application of this process are high operating temperature (>200° C.), deactivation of catalyst due to coke formation, limited availability and high cost of $N_2O$ oxidant. Another process using divalent iron as catalyst and hydrogen peroxide as oxidant has been reported for direct hydroxylation of benzene to phenol (J. Chem. Soc. 1969, 2897). Another process for direct hydroxylation of benzene to phenol describes the oxidation of benzene with $H_2$ and $O_2$ using a palladium catalyst supported on TS-1 (J. Chem. Soc. Chem. Comm. 1992, 1446). Yet another process describes the use of molecular oxygen as oxidant and poly (metal) salt of dihyroxyanthraquinone dissolved in water as catalyst for direct hydroxylation of benzene to phenol (U.S. Pat. No. 4,982,600). Still another process describes the synthesis of phenol by catalytic one step oxidation of benzene using TS-1 as catalyst and hydrogen peroxide (prepared insitu by reaction of $O_2$, CO and water in presence of palladium complex as catalyst) as oxidant (U.S. Pat. No. 5,981,764). Still another process described the use of ammonium salt of mono vanadium (V) substituted heteropoly amines as catalysts for direct hydroxylation of benzene to phenol with hydrogen peroxide (J. Mol. Catal. A: Chem. 1991, 67, 7). Yet another process for Liquid phase direct hydroxylation of benzene to phenol using titanium and vanadium containing zeolites as catalysts and hydrogen peroxide as oxidant have been reported (J. Mol. Catal. 1992; Micro. Mater. 1994, 2, 451). Another literature report (J. Mol. Catal. 1997, 126, 43) describes a process for one step oxidation of benzene to phenol wherein, a mesoporous molecular sieve, MCM-41 either exchanged with copper ions or loaded with copper oxide was used as the catalyst, 10 atmospheric pressure of oxygen as oxidant, ascorbic acid as reducing agent and acetic acid as solvent. A recent, U.S. Pat. No. 6,180,836 B discloses a process for direct liquid phase hydroxylation of benzene to phenol, which involves the use of hydrogen peroxide as oxidant and molecular sieves doped with copper ion as catalyst. Another recent report (J. Mol. Catal. 2000, 156, 143), describes direct hydroxylation of benzene to phenol by using hydrogen peroxide as oxidant and vanadium (V) substituted polyoxomolybdates as catalysts. Yet another literature report (J. Mol. Catal. 2006, 253, 1) describes sodium metavanadate catalyzed direct hydroxylation of benzene to phenol using hydrogen peroxide as oxidant and acetonitrile as solvent. Still another literature report (Appl. Clay Sci. 2006, 33, 1) describes the selective hydroxylation of benzene to phenol using hydrogen peroxide as oxidant and clay supported vanadium oxide as catalyst. Yet another literature report (Catal. Today 1999, 49, 285) describes direct hydroxylation of benzene to phenol, toluene to cresols and anisole to methoxyphenols under solvent free triphasic conditions using TS-1 as catalyst and $H_2O_2$ as oxidant.

A process for direct hydroxylation of toluene to cresols by using $N_2O$ as oxidant and pentasil or β-type zeolites as catalysts with conversion rate 24% and selectivity 24% have been reported in DE A-196,34,406. Another process for direct hydroxylation of toluene to cresols by using dinitrogen monooxide ($N_2O$) as oxidant, iron-containing zeolite as catalyst in the temperature range 275 to 450° C. has been reported (U.S. Pat. No. 5,110,995) and conversion rate 48% with selectivity for cresol 20% have been achieved. Another process for direct hydroxylation of toluene to cresols by using zeolites which have been passed through a special two stage calcinations process as catalyst, $N_2O$ as oxidant with conversion rate 25% and selectivity for cresol 22% has been reported (EPA 889, 081). Yet another patent (U.S. Pat. No. 6,476,277 B2) describes a process for direct hydroxylation of toluene to cresols by using nanocrysatline zeolites as catalysts and $N_2O$ as oxidant.

A process for direct hydroxylation of anisole to methoxyphenols with $H_2O_2$ in $CF_3SO_3H$ containing small amount of $H_3PO_4$ has been described in U.S. Pat. Nos. 4,223,165 and 4,301,307. Another process where phenolic ethers and phenol derivatives have been directly hydroxylated with hydrogen peroxide in the presence of acidic clays has been described in EP 314, 583. Yet another process for direct hydroxylation of anisole to methoxyphenols with $H_2O_2$ in presence of titanosilicate catalyst and cyclic ethers like THF, dioxane as solvent has been described in U.S. Pat. No 5,426,244.

The drawbacks of the hitherto known processes such as lower activity of the catalyst, less conversion, poor selectivity, evident the necessity for development of an improved process for direct hydroxylation of aromatic hydrocarbons like benzene, toluene and anisole.

OBJECTIVES OF THE PRESENT INVENTION

The main object of the present invention is to provide a process for direct hydroxylation of aromatic hydrocarbons.

Another object of the present invention is to provide a process for the direct liquid phase hydroxylation of aromatic hydrocarbons like benzene to phenol, toluene to cresols and anisole to methoxyphenols with hydrogen peroxide as oxidant by using vanadium based catalysts particularly vanadyl phthalocyanine, under mild reaction conditions.

Yet another object of the present invention is to provide a process for direct hydroxylation of aromatic hydrocarbons using hydrogen peroxide as environmentally benign oxidant.

Still another object of the present invention is to provide a process for the hydroxylation of aromatic hydrocarbons like benzene to phenol, toluene to cresols, anisole to methoxyphenols by using vanadium based catalysts particularly vanadyl phthalocyanine.

SUMMARY OF THE INVENTION

Accordingly the present invention provides a process for direct hydroxylation of aromatic hydrocarbons which comprises reacting aromatic hydrocarbon with hydrogen peroxide with a molar ratio of hydrocarbon to hydrogen peroxide in the range 1:0.05 to 1:10 in a polar solvent with a weight ratio of hydrocarbon to solvent in the range 1:3 to 1:20, in the presence of heterogeneous catalyst selected from vanadium phthalocyanine or its derivative, at a temperature in the range of 25-100° C., for a period 1-10 hrs in a batch or continuous manner, removing the catalyst from the above said reaction mixture, followed by fractional distillation of the resultant filtrate to recover the unreacted aromatics and obtaining the desired hydroxyl aromatics.

In an embodiment of the present invention the aromatic hydrocarbon used for hydroxylation is selected from the group consisting benzene, toluene, anisole, xylene, trimethylbenzene and cyclohexane.

In yet another embodiment the hydrogen peroxide used is selected from the group consisting of 5-60 wt % aqueous $H_2O_2$, urea-$H_2O_2$ adduct, $H_2O_2$-alkali metal borate adduct and $H_2O_2$-alkali carbonate adduct.

In yet another embodiment the alkali metal used is selected from the group consisting of sodium, potassium, magnesium, calcium, barium and strontium.

In yet another embodiment the mole ratio of aromatic hydrocarbon to hydrogen peroxide used is preferably in the range from 1:1 to 1:5.

In yet another embodiment the weight ratio of aromatic hydrocarbon to solvent used is preferentially in the range 1:4 to 1:15.

In yet another embodiment the polar solvent used is selected from the group consisting of methanol, acetone, water and acetonitrile.

In yet another embodiment the mole ratio of vanadium based catalyst to substrate used is preferably in the range of 2 to 5 mol %.

In yet another embodiment the derivative of vanadyl phthalocyanine catalyst used is selected from phenoxy, nitro, chloro and amino substituted vanadyl phthalocyanine.

In yet another embodiment the of vanadyl phthalocyanine catalyst used is supported on any of the material selected from polymer, biomaterial, silica, mesoporous silica materials or encapsulated in zeolites.

In yet another embodiment the reaction temperature used is preferably in the range of 50-80° C.

In yet another embodiment the reaction time used for hydroxylation of aromatics is preferably in the rage of 5-10 hrs.

In yet another embodiment the conversion of the aromatics to hydroxy aromatics obtained is probably in the range 15-50%.

In still another embodiment the selectivity of phenol in the hydroxylation of benzene is 100% without any side product.

DETAILED DESCRIPTION OF THE PRESENT INVENTION

According to the present invention, to a solution of aromatic hydrocarbon (0.05 mol) in acetonitrile (4 to 15 times weight of aromatic hydrocarbon) contained in a 100 ml round bottomed flask 30/50% aqueous solution of hydrogen peroxide (0.05 to 0.25 mole) was added at room temperature. To the reaction mixture vanadium based catalyst (2 to 5 mol % of aromatic hydrocarbon) was then added. The resulting reaction mixture was heated to 50-80° C. under vigorous stirring conditions. The stirring was continued at the same temperature for 5-10 h followed by removal of catalyst by filtration on Buchner funnel or passing the reaction mixture through a small silica gel column or both. The reaction mixture thus obtained was evaporated under reduced pressure and the residue left was weighted and analyzed by high resolution GCMSD EI, quadrapole mass analyzer, EM detector. The conversion of aromatic hydrocarbons to hydroxy aromatics as determined on the basis of weight of the residue left after evaporation under vacuum remained 10-50%. The product selectivity was determined by GCMSD. As stated above, the invention provides a process for liquid phase direct hydroxylation of aromatic hydrocarbons to hydroxy aromatics using hydrogen peroxide as oxidant, acetonitrile as solvent in presence of vanadium based catalyst in the temperature range of 50-80° C.

The following examples are given by the way of illustration and therefore should not be construed to limit the scope of the present invention.

EXAMPLE 1

In to a 100 ml round-bottomed double necked flask containing, benzene (0.05 mol, 3.9 g), 50% aq. hydrogen peroxide (0.05 mol, 3.4 g) in acetonitrile (20 ml) was added vanadyl tetraphenoxyphthalocyanine (2.5 mol %, 1.18 g). The reaction was continued with vigorous stirring at 65° C. for 8 h. The reaction mixture was then filtered through a Buckner funnel, passed through a short column of silica gel to remove the catalyst and concentrated under reduced pressure. The resulting residue was analyzed by high resolution GCMSD, EI, quadrapole mass analyzer, EM detector. The conversion of benzene to phenol was determined on the basis of the weight of the residue left after evaporation and selectivity for phenol formation was determined by GC. Conversion of benzene to phenol was 22.4%. The selectivity for phenol was 100%.

EXAMPLE 2

In to a 100 ml round-bottomed double-necked flask containing benzene (0.05 mol, 3.9 g), 50% aq. hydrogen peroxide (0.1 mol, 6.8 g) in acetonitrile (30 ml) was added vanadyl tetraphenoxyphthalocyanine (2.5 mol %, 1.18 g). The reaction was continued with vigorous stirring at 65° C. for 8 h. The reaction mixture was then filtered through a Buckner funnel, passed through a short column of silica gel to remove the catalyst and concentrated under reduced pressure. The resulting residue was analyzed by high resolution GCMSD, EI, quadrapole mass analyzer, EM detector. The conversion of benzene to phenol was determined on the basis of the weight of the residue left after evaporation and selectivity for phenol formation was determined by GC. Conversion of benzene to phenol was 33.19%. The selectivity for phenol was 100%.

EXAMPLE 3

In to a 150 ml round-bottomed double-necked flask containing, benzene (0.05 mol, 3.9 g), 50% aq. hydrogen peroxide (0.25 mol, 17.0 g) in acetonitrile (50 ml) was added vanadyl tetraphenoxyphthalocyanine (2.5 mol %, 1.18 g). The reaction was continued with vigorous stirring at 65° C. for 8 h. The reaction mixture was then filtered through a Buckner funnel, passed through a short column of silica gel to remove the catalyst and concentrated under reduced pressure. The resulting residue was analyzed by high resolution GCMSD, EI, quadrapole mass analyzer, EM detector. The conversion of benzene to phenol was determined on the basis of the weight of the residue left after evaporation and selectivity for phenol formation was determined by GC. Conversion of benzene to phenol was 41.49%. The selectivity for phenol was 100%.

EXAMPLE 4

In to a 100 ml round-bottomed double-necked flask containing toluene (0.05 mol, 4.6 g), 50% aq. hydrogen peroxide (0.05 mol, 3.4 g) in acetonitrile (20 ml) was added vanadyl tetraphenoxyphthalocyanine (2.5 mol %, 1.18 g). The reaction was continued with vigorous stirring at 65° C. for 8 h. The reaction mixture was then filtered through a Buckner funnel, passed through a short column of silica gel to remove the catalyst and concentrated under reduced pressure. The resulting residue was analyzed by high resolution GCMSD, EI, quadrapole mass analyzer, EM detector. The conversion of toluene was determined on the basis of the weight of the residue left after evaporation and selectivities for m, p- and o-cresols were determined by GC. Conversion of toluene was 18.74%. The selectivity for m, p-cresol was 57%. The selectivity for o-cresol was 38%.

EXAMPLE 5

In to a 100 ml round-bottomed double-necked flask containing, toluene (0.05 mol, 4.6 g), 50% aq. hydrogen peroxide (0.1 mol, 6.8 g) in acetonitrile (30 ml) was added vanadyl tetraphenoxyphthalocyanine (2.5 mol %, 1.18 g). The reaction was continued with vigorous stirring at 65° C. for 8 h. The reaction mixture was then filtered through a Buckner funnel, passed through a short column of silica gel to remove the catalyst and concentrated under reduced pressure. The resulting residue was analyzed by high resolution GCMSD, EI, quadrapole mass analyzer, EM detector. The conversion of toluene was determined on the basis of the weight of the residue left after evaporation and selectivities for m, p- and o-cresols were determined by GC. Conversion of toluene was 28.9%. The selectivity for m, p-cresol was 56%. The selectivity for o-cresol was 39%.

EXAMPLE 6

In to a 150 ml round-bottomed double-necked flask containing toluene (0.05 mol, 4.6 g), 50% aq. hydrogen peroxide (0.25 mol, 17.0 g) in acetonitrile (50 ml) was added vanadyl tetraphenoxyphthalocyanine (2.5 mol %, 1.18 g). The reaction was continued with vigorous stirring at 65° C. for 8 h. The reaction mixture was then filtered through a Buckner funnel, passed through a short column of silica gel to remove the catalyst and concentrated under reduced pressure. The resulting residue was analyzed by high resolution GCMSD, EI, quadrapole mass analyzer, EM detector. The conversion of toluene was determined on the basis of the weight of the residue left after evaporation and selectivities for m, p- and o-cresols were determined by GC. Conversion of toluene was 34.9%. The selectivity for m, p-cresol was 56.5%. The selectivity for o-cresol was 38.5%.

EXAMPLE 7

In to a 150 ml round-bottomed double-necked flask containing anisole (0.05 mol, 5.4 g), 50% aq. hydrogen peroxide (0.25 mol, 17.0 g) in acetonitrile (50 ml) was added vanadyl tetraphenoxyphthalocyanine (2.5 mol %, 1.18 g). The reaction was continued with vigorous stirring at 65° C. for 8 h. The reaction mixture was then filtered through a Buckner funnel, passed through a short column of silica gel to remove the catalyst and concentrated under reduced pressure. The resulting residue was analyzed by high resolution GCMSD, EI, quadrapole mass analyzer, EM detector. The conversion of anisole was determined on the basis of the weight of the residue left after evaporation and yields of guaiacol and 4-methoxyphenol were determined by GC. Conversion of anisole was 18%. The yield of the mixture of guaiacol and 4-methoxyphenol was 17.5%.

Examples 8-15 are herein given below as comparative examples.

EXAMPLE 8

In to a 100 ml round-bottomed double-necked flask containing benzene (0.05 mol, 3.9 g), 50% aq. hydrogen peroxide (0.05 mol, 3.4 g) in acetonitrile (20 ml) was added vanadyl acetylacetonate (2.5 mol %, 0.33 g). The reaction was continued with vigorous stirring at 65° C. for 8 h. After completion of the reaction, the reaction mixture was passed through a short column of silica gel to remove the catalyst and concentrated under reduced pressure. The resulting residue was analyzed by high resolution GCMSD, EI, quadrapole mass analyzer, EM detector. The conversion of benzene to phenol was determined on the basis of the weight of the residue left after evaporation and selectivity for phenol formation was determined by GC. Conversion of benzene was 11%. The selectivity for phenol was 100%.

EXAMPLE 9

In to a 100 ml round-bottomed double-necked flask containing benzene (0.05 mol, 3.9 g), 50% aq. hydrogen peroxide (0.1 mol, 6.8 g) in acetonitrile (30 ml) was added vanadyl acetylacetonate (2.5 mol %, 0.33 g). The reaction was continued with vigorous stirring at 65° C. for 8 h. After completion of the reaction, the reaction mixture was passed through a short column of silica gel to remove the catalyst and concentrated under reduced pressure. The resulting residue was analyzed by high resolution GCMSD, EI, quadrapole mass analyzer, EM detector. The conversion of benzene to phenol was determined on the basis of the weight of the residue left after evaporation and selectivity for phenol formation was determined by GC. Conversion of benzene was 18.25%. The selectivity for phenol was 100%.

EXAMPLE 10

In to a 150 ml round-bottomed double-necked flask containing benzene (0.05 mol, 3.9 g), 50% aq. hydrogen peroxide (0.25 mol, 17.0 g) in acetonitrile (50 ml) was added vanadyl acetylacetonate (2.5 mol %, 0.33 g). The reaction was continued with vigorous stirring at 65° C. for 8 h. After completion of the reaction, the reaction mixture was passed through a short column of silica gel to remove the catalyst and concentrated under reduced pressure. The resulting residue was analyzed by high resolution GCMSD, EI, quadrapole mass analyzer, EM detector. The conversion of benzene to phenol was determined on the basis of the weight of the residue left after evaporation and selectivity for phenol formation was determined by GC. Conversion of benzene was 33.19%. The selectivity for phenol was 100%.

EXAMPLE 11

In to a 100 ml round-bottomed double-necked flask containing toluene (0.05 mol, 4.6 g), 50% aq. hydrogen peroxide (0.1 mol, 6.8 g) in acetonitrile (30 ml) was added vanadyl acetylacetonate (2.5 mol %, 0.33 g). The reaction was continued with vigorous stirring at 65° C. for 8 h. After completion of the reaction, the reaction mixture was passed through a short column of silica gel to remove the catalyst and concentrated under reduced pressure. The resulting residue was analyzed by high resolution GCMSD, EI, quadrapole mass analyzer, EM detector. The conversion of toluene was determined on the basis of the weight of the residue left after evaporation and selectivities for m, p- and o-cresols were determined by GC. Conversion of toluene was 10%. The selectivity for m, p-cresol was 56%. The selectivity for o-cresol was 37%.

EXAMPLE 12

In to a 100 ml round-bottomed double-necked flask containing, benzene (0.05 mol, 3.9 g), 50% aq. hydrogen peroxide (0.1 mol, 6.8 g) in acetonitrile (30 ml) was added 20% $V_2O_5/Al_2O_3$ (2.5 mol %, 1.3 g) (Appl. Catal., 1988, 40, 191). The reaction was continued with vigorous stirring at 65° C. for 8 h. The reaction mixture was then filtered through a Buckner funnel to remove the catalyst and concentrated under reduced pressure. The resulting residue was analyzed by high resolution GCMSD, EI, quadrapole mass analyzer, EM detector. The conversion of benzene to phenol was determined on the basis of the weight of the residue left after evaporation and selectivity for phenol formation was determined by GC. Conversion of benzene was 18%. The selectivity for phenol was 93% (Hydroquinone 7%).

EXAMPLE 13

In to a 100 ml round-bottomed double-necked flask containing, toluene (0.05 mol, 4.6 g), 50% aq. hydrogen peroxide (0.1 mol, 6.8 g) in acetonitrile (30 ml) was added 20% $V_2O_5/Al_2O_3$ (2.5 mol %, 1.13 g. The reaction was continued with vigorous stirring at 65° C. for 8 h. The reaction mixture was then filtered through a Buckner funnel to remove the catalyst and concentrated under reduced pressure. The resulting residue was analyzed by high resolution GCMSD, EI, quadrapole mass analyzer, EM detector. The conversion of toluene was determined on the basis of the weight of the residue left after evaporation and selectivities for m, p- and o-cresols were determined by GC. Conversion of toluene was 8%. The selectivity for m, p-cresol was 68%. The selectivity for o-cresol was 20%.

EXAMPLE 14

In to a 100 ml round-bottomed double-necked flask containing, benzene (0.05 mol, 3.9 g), 50% aq. hydrogen peroxide (0.1 mol, 6.8 g) in acetonitrile (30 ml) was added 14% $V_2O_5/TiO_2$ (2.5 mol %, 1.62 g (Langmuir 2000, 16, 7192). The reaction was continued with vigorous stirring at 65° C. for 8 h. The reaction mixture was then filtered through a Buckner funnel to remove the catalyst and concentrated under reduced pressure. The resulting residue was analyzed by high resolution GCMSD, EI, quadrapole mass analyzer, EM detector. The conversion of benzene to phenol was determined on the basis of the weight of the residue left after evaporation and selectivity for phenol formation was determined by GC. Conversion of benzene was 10%. The selectivity for phenol was 91% (hydroquinone 9%).

EXAMPLE 15

In to a 100 ml round-bottomed double-necked flask containing, benzene (0.05 mol, 3.9 g), 50% aq. hydrogen peroxide (0.1 mol, 6.8 g) in acetonitrile (30 ml) was added 11% $V_2O_5/ZrO_2$ (2.5 mol %, 2.06 g) (J. Mol. Catal. 1990, 58, L13). The reaction was continued with vigorous stirring at 65° C. for 8 h. The reaction mixture was then filtered through a Buckner funnel to remove the catalyst and concentrated under reduced pressure. The resulting residue was analyzed by high resolution GCMSD, EI, quadrapole mass analyzer, EM detector. The conversion of benzene to phenol was determined on the basis of the weight of the residue left after evaporation and selectivity for phenol formation was determined by GC. Conversion of benzene to phenol was 12%. The selectivity for phenol was 92% (hydroquinone 7.5%, p-benzoquinone 0.5%).

EXAMPLE 16

In to a 150 ml round-bottomed double-necked flask containing, benzene (0.05 mol, 3.9 g), 50% aq. hydrogen peroxide (0.25 mol, 17.0 g) in acetonitrile (50 ml) was added recovered vanadyl tetraphenoxyphthalocyanine (Run 2). The reaction was continued with vigorous stirring at 65° C. for 8 h. The reaction mixture was then filtered through a Buckner funnel, passed through a short column of silica gel to remove the catalyst and concentrated under reduced pressure. The resulting residue was analyzed by high resolution GCMSD, EI, quadrapole mass analyzer, EM detector. The conversion of benzene to phenol was determined on the basis of the weight of the residue left after evaporation and selectivity for phenol formation was determined by GC. Conversion of benzene to phenol was 40.14%. The selectivity for phenol was 100%.

EXAMPLE 17

In to a 150 ml round-bottomed double-necked flask containing, benzene (0.05 mol, 3.9 g), 50% aq. hydrogen peroxide (0.25 mol, 17.0 g) in acetonitrile (50 ml) was added recovered vanadyl tetraphenoxyphthalocyanine (Run 3). The reaction was continued with vigorous stirring at 65° C. for 8 h. The reaction mixture was then filtered through a Buckner funnel, passed through a short column of silica gel to remove the catalyst and concentrated under reduced pressure. The resulting residue was analyzed by high resolution GCMSD, EI, quadrapole mass analyzer, EM detector. The conversion of benzene to phenol was determined on the basis of the weight of the residue left after evaporation and selectivity for phenol formation was determined by GC. Conversion of benzene to phenol was 39.15%. The selectivity for phenol was 100%.

ADVANTAGES OF THE PRESENT INVENTION

The present process is uniformly applicable for a wide variety of aromatic hydrocarbons like benzene, toluene and anisole.

The present invention describes for first time use of vanadyl phthalocyanine as highly active catalyst for hydroxylation of aromatic hydrocarbons like benzene, toluene, anisole which could be recycled without any metal leaching problem.

In the present invention hydroxylation of aromatic hydrocarbons is carried out under very mild reaction conditions by using environmentally benign aqueous hydrogen peroxide as oxidant.

In the present invention the obtained conversion for benzene to phenol and toluene to cresols are better than other processes reported in the literature using hydrogen peroxide/ molecular oxygen as oxidant.

In the present invention the obtained selectivity for phenol in hydroxylation of benzene remains 100% even at high conversion which has not been achieved earlier.

In the present invention the conversions for the hydroxylation of toluene to cresols were found to be significantly high with good selectivities for m, p-cresol. This is highly advantageous as toluene is cheaper raw material than phenol.

The invention claimed is:

1. A process for direct hydroxylation of aromatic hydrocarbons which comprises reacting aromatic hydrocarbon with hydrogen peroxide with a molar ratio of aromatic hydrocarbon to hydrogen peroxide in the range 1:0.05 to 1:10 in a polar solvent with a weight ratio of aromatic hydrocarbon to solvent in the range 1:3 to 1:20, in the presence of heterogeneous catalyst selected from a group consisting of vanadium phthalocyanine and phenoxy-, nitro-, chloro-, and amino-substituted vanadiyl phthalocyanine, at a temperature in the range of 25-100° C., for a period 1-10 hrs in a batch or continuous manner, removing the catalyst from the above said reaction mixture, followed by fractional distillation of the resultant filtrate to recover the unreacted aromatics and obtaining the desired hydroxyl aromatics.

2. A process according to claim 1, wherein the aromatic hydrocarbon used for hydroxylation is selected from the group consisting of benzene, toluene, anisole, xylene, trimethylbenzene and cyclohexane.

3. A process according to claim 1, wherein the hydrogen peroxide used is selected from the group consisting of 5-60 wt % aqueous $H_2O_2$, urea-$H_2O_2$ adduct, $H_2O_2$-alkali metal borate adduct and $H_2O_2$-alkali carbonate adduct.

4. A process according to claim 3, wherein the alkali metal used is selected from the group consisting of sodium, potassium, magnesium, calcium, barium and strontium.

5. A process according to claim 1, wherein the mole ratio of aromatic hydrocarbon to hydrogen peroxide used is in the range from 1:1 to 1:5.

6. A process according to claim 1, wherein the weight ratio of aromatic hydrocarbon to solvent used is in the range 1:4 to 1:15.

7. A process according to claim 1, wherein the polar solvent used is selected from the group consisting of methanol, acetone, water and acetonitrile.

8. A process according to claim 1, wherein a mole ratio of catalyst to substrate used is in the range of 2 to 5 mol %.

9. A process according to claim 1, wherein the of vanadyl phthalocyanine catalyst used is supported on any of the material selected from polymer, biomaterial, silica, mesoporous silica materials or encapsulated in zeolites.

10. A process according to claim 1, wherein the reaction temperature used is in the range of 50-80° C.

11. A process according to claim 1, wherein the reaction time used for hydroxylation of aromatics is in the range of 5-10 hrs.

12. A process according to claim 1, wherein the conversion of the aromatics to hydroxy aromatics obtained is in the range 15-50%.

13. A process according to claim 1, wherein the selectivity of phenol in the hydroxylation of benzene is 100% without any side product.

* * * * *